United States Patent [19]
Glantz et al.

[11] Patent Number: 5,387,192
[45] Date of Patent: Feb. 7, 1995

[54] HYBRID PORTAL AND METHOD

[75] Inventors: Jerald Glantz, Lake Elmo; Mark D. Anderson, Stacy; Theodore A. Johnson, St. Paul; William L. Beling, New Brighton; Cai Qingsheng, St. Paul, all of Minn.

[73] Assignee: SIMS Deltec, Inc., St. Paul, Minn.

[21] Appl. No.: 186,171

[22] Filed: Jan. 24, 1994

[51] Int. Cl.⁶ ............................................. A61M 5/00
[52] U.S. Cl. ........................................ 604/93; 604/49; 604/167
[58] Field of Search ............... 604/93, 167, 174, 175, 604/49, 82, 83, 86, 252, 256

[56] References Cited

U.S. PATENT DOCUMENTS

| | | |
|---|---|---|
| 4,452,473 | 6/1984 | Ruschke . |
| 4,557,722 | 12/1985 | Harris . |
| 4,588,394 | 5/1986 | Schulte et al. . |
| 4,592,749 | 6/1986 | Ebling et al. . |
| 4,655,765 | 4/1987 | Swift . |
| 4,673,394 | 6/1987 | Fenton, Jr. . |
| 4,675,007 | 6/1987 | Terry . |
| 4,704,103 | 11/1987 | Stober et al. . |
| 4,710,174 | 12/1987 | Moden et al. . |
| 4,723,948 | 2/1988 | Clark et al. . |
| 4,738,657 | 4/1988 | Hancock et al. . |
| 4,767,410 | 8/1988 | Moden et al. . |
| 4,772,270 | 9/1988 | Wiita et al. . |
| 4,772,276 | 9/1988 | Wiita et al. . |
| 4,778,452 | 10/1988 | Moden et al. . |
| 4,781,680 | 11/1988 | Redmond et al. . |
| 4,781,685 | 11/1988 | Lehman et al. . |
| 4,802,885 | 2/1989 | Weeks et al. . |
| 4,838,873 | 6/1989 | Landskron et al. . |
| 4,838,887 | 6/1989 | Idriss . |
| 4,840,615 | 6/1989 | Hancock et al. . |
| 4,861,341 | 8/1989 | Woodburn . |
| 4,871,351 | 10/1989 | Feingold . |
| 4,880,414 | 11/1989 | Whipple . |
| 4,892,518 | 1/1990 | Cupp et al. . |
| 4,904,241 | 2/1990 | Bark . |
| 4,915,690 | 4/1990 | Cone et al. . |
| 4,929,236 | 5/1990 | Sampson . |
| 4,963,133 | 10/1990 | Whipple . |
| 4,978,338 | 12/1990 | Melsky et al. . |
| 4,994,048 | 2/1991 | Metzger . |
| 5,013,298 | 5/1991 | Moden et al. . |
| 5,026,344 | 6/1991 | Dijkstra et al. . |
| 5,041,098 | 8/1991 | Loiterman et al. . |
| 5,045,060 | 9/1991 | Melsky et al. . |
| 5,085,644 | 2/1992 | Watson et al. . |
| 5,090,954 | 2/1992 | Geary . |
| 5,092,849 | 3/1992 | Sampson . |
| 5,108,377 | 4/1992 | Cone et al. . |
| 5,129,891 | 7/1992 | Young . |
| 5,137,529 | 8/1992 | Watson et al. . |
| 5,147,483 | 9/1992 | Melsky et al. . |
| 5,149,330 | 9/1992 | Brightbill . |
| 5,167,638 | 12/1992 | Felix et al. . |
| 5,171,228 | 12/1992 | McDonald . |
| 5,178,612 | 1/1993 | Fenton, Jr. . |
| 5,180,365 | 1/1993 | Ensminger et al. . |
| 5,185,003 | 2/1993 | Brethauer . |
| 5,213,574 | 5/1993 | Tucker . |
| 5,281,199 | 1/1994 | Ensminger et al. ................ 604/93 |
| 5,312,337 | 5/1994 | Flaherty et al. . |
| 5,318,545 | 6/1994 | Tucker . |
| 5,336,194 | 8/1994 | Polaschegg et al. ............. 604/175 |

FOREIGN PATENT DOCUMENTS 0258777  3/1988  European Pat. Off. .

OTHER PUBLICATIONS

"DAVOL Implanted Ports with Groshong ™ Catheter—Use and Maintenance", Bard Access Systems, Salt Lake City, Utah; Feb. 1992.

(List continued on next page.)

Primary Examiner—John D. Yasko
Attorney, Agent, or Firm—Merchant, Gould, Smith, Edell, Welter & Schmidt

[57] ABSTRACT

The present invention provides an subcutaneously implantable access device including a metallic reservoir and a two piece plastic jacket. The metallic reservoir includes a sealed septum, and a chamber. The chamber is accessible through the septum. A two piece plastic jacket surrounds the metallic reservoir. The two piece jacket includes a cowl and a base connected to one another around the reservoir. A dual port construction is also provided.

34 Claims, 11 Drawing Sheets

OTHER PUBLICATIONS

"Implanted Ports with Hickman ® Catheter—Use and Maintenance", Bard Access Systems, Salt Lake City, Utah; Feb. 1992.

Photograph: CELSA product.

"Chemo-Port ® Implantable Vascular Access Ports", HDC Corporation, San Jose, Calif.; 1991.

"TrimPort TM Series Superior Vascular Access", Gerard Medical, Inc., Massachusetts; undated.

"For secure fluid delivery to vascular access ports," Gish Biomedical, Inc., Irvine, Calif.; Mar.–Apr. 1993.

"A-Port TM Implantable Vascular Access System", Therex Corporation, Walpole, Mass.; 1992.

"Vascular Access Products", Strato Medical Corporation/Pfizer, Beverly, Mass.; Sep. 1991.

"NORPORT TM -LS Vascular-Access Port", Norfolk Medical, Skokie, Ill.; undated.

"OMEGAPORT TM Implantable Access System for All Therapies", Norfolk Medical, Skokie, Ill.; Jan. 1, 1992.

"SURE CATH ® Port Access Catheter", Ivion Corporation, Broomfield, Colo.; 1992.

"Access Ability—the S.E.A.-Port ® Topsider TM ", Harbor Medical Devices, Inc., Jaffrey, N.H.; 1991.

"Turning Vascular Access on its Side—S.E.A.-Port TM ", Harbor Medical Devices, Inc., Jaffrey, N.H.; undated.

"Covering the Angles on Access", Harbor Medical Devices, Inc., Jaffrey, N.H.; 1989.

"The Key to a Good Vascular Access Port System is Using the Right Combination.", Gish Biomedical, Inc., Irvine, Calif.; 1987.

"ImPort TM —Vascular Access Port", Pudenz-Schulte Medical Corporation, Goleta, Calif.; undated.

"Functionally Superior", Therex Corporation, Walpole, Mass.; 1992.

"Dimensionally Distinctive", Therex Corporation, Walpole, Mass.; undated.

"Oncology/Critical Care", Quinton Instrument Company (an A. H. Robins Company), Seattle, Wash.; Jul. 1988.

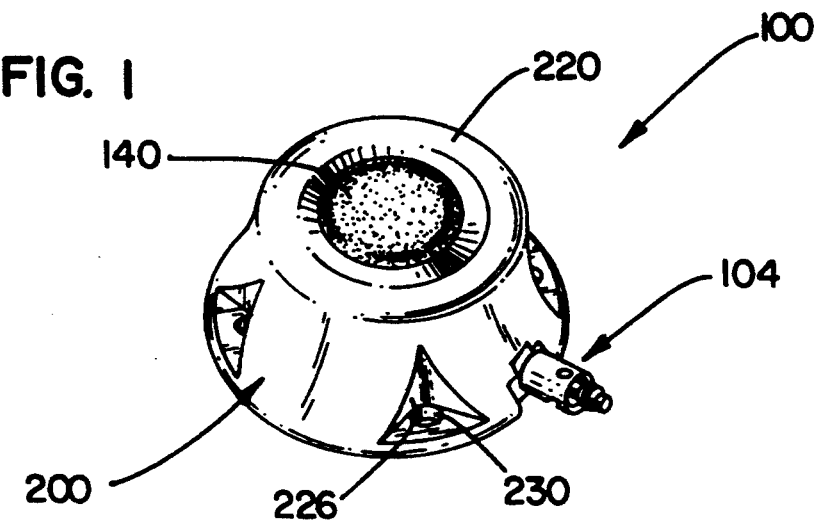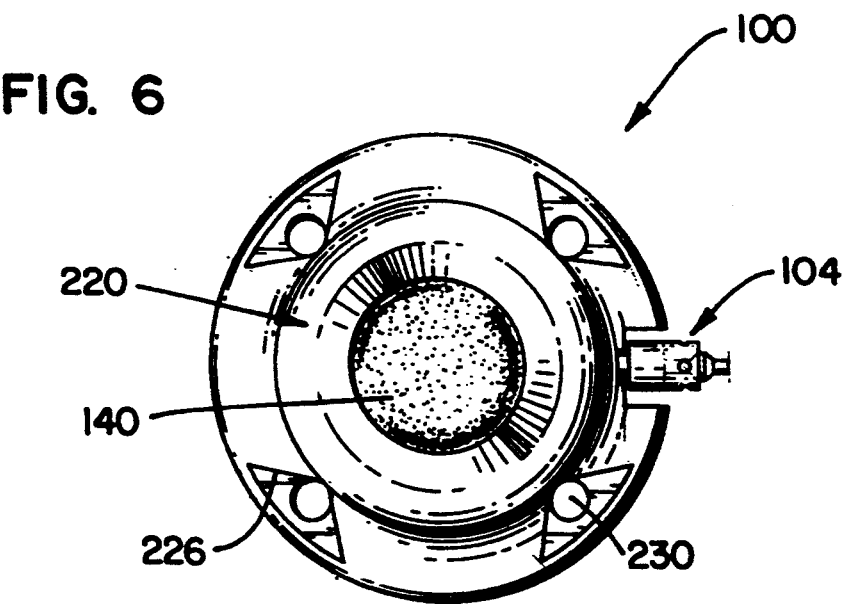

HYBRID PORTAL AND METHOD

TECHNICAL FIELD

The present invention relates to implantable biocompatible access devices used in connection with the delivery of medicants, and other pharmaceutical fluids into a body, or the withdrawal of fluids from the body.

BACKGROUND OF THE INVENTION

Access portals, or ports, provide a convenient method to repeatedly deliver medicants to remote areas of the body without utilizing surgical procedures. The port is totally implantable within the body, and permits the infusion of medications, parenteral solutions, blood products, and other fluids. The port may also be used for blood sampling.

Known ports typically include a chamber accessible through a self-sealing septum. Septums of the prior art vary in shape, from a wafer-like cylindrical block of silicone to a pre-molded septum of U.S. Pat. No. 4,802,885 to Weeks et al. The pre-molded septum of U.S. Pat. No. 4,802,885 includes opposed convex surfaces and a peripheral ledge.

In common practice, a caregiver locates the septum of the port by palpitation. Port access is accomplished by percutaneously inserting a needle, typically a non-coring needle, perpendicularly through the septum of the port and into the chamber. The drug or fluid is then administered by bolus injection or continuous infusion. Ordinarily the fluid flows through the chamber, into a catheter and finally to the site were the fluid is desired.

Except for the septum, traditional ports are constructed from all-metal or all-plastic. Each type of construction has unique advantages and disadvantages.

All-metal constructions have the advantages that they maintain a septum in a self-sealing fashion after repeated percutaneous injections. Additionally, all-metal constructions, such as titanium, or stainless steel provide a port which is both biocompatible and compatible with the injected fluid.

However, all-metal constructions present the disadvantages that they are relatively heavy, difficult to fabricate and relatively expensive. Additionally, all-metal ports produce large Magnetic Resonance Imaging (MRI) artifacts.

On the other hand, all-plastic ports have the advantages that they are inexpensive to construct, light in weight, and do not create an MRI artifact. However, ports constructed from plastic have the disadvantage that infused fluids may react with the plastic body of the port. All-plastic ports contain the disadvantage that they cannot maintain a sealing engagement with the septum after repeated percutaneous injections. Additionally, all-plastic ports are susceptible to nicks and scratches on the interior surface by the accessing needle. These nicks and scratches could lead to nidus, blood clots, or precipitation formations.

Efforts have been made to combine the advantages of all-metal ports with all-plastic ports. For example, in U.S. Pat. No. 4,802,885 to Weeks et al., a metal reservoir having a chamber sealed by a pre-formed silicone septum is jacketed by a single piece of a silicone elastomer. However, all-metal ports jacketed by a single piece of elastomer have significant shortcomings. These shortcomings include quality control problems during manufacturing, and expensive molding processes.

Other efforts have focused on providing a multiple piece all-plastic housing in cooperation with an open metal cup to sealingly engage a septum. For example, see U.S. Pat. No. 5,213,574 to Tucker. This design has shortcomings associated with it, including defects in the plastic housing which may cause an improperly sealed septum. Once the septum is improperly sealed the entire port must be discarded.

Therefore a need has arisen for an access port device which addresses the problems of prior port devices.

SUMMARY OF THE INVENTION

A hybrid port is provided which includes a metallic reservoir, a non-metallic cowl and a non-metallic base. The metallic reservoir has an open top, a closed bottom and a septum. The open top is sealed by the septum to define a chamber. The non-metallic cowl includes a septum opening. The cowl also includes a flange which is positioned adjacent to the top of the reservoir, so that the septum is accessible through the septum opening. The non-metallic base includes a reservoir opening, in which the reservoir is operably received through. The cowl and the base are positioned and arranged to define a forming zone. The cowl and base are connected at the forming zone to substantially surround the reservoir.

A dual hybrid port is also provided. The dual hybrid port includes a metallic reservoir including two chambers, each of the chambers accessible through a discrete septum. A non-metallic cowl which includes a discrete pair of septum openings, and a discrete pair of flanges, each of the flanges positioned adjacent one of the septum openings is positioned so that each septum is accessible through one of the septum openings. A non-metallic base is also provided. The non-metallic base has a reservoir opening positioned to receive the reservoir therethrough. The base and the cowl are positioned and arranged to define a forming zone and the base and cowl are connected at the forming zone.

A method of using a hybrid port is also provided. The method includes steps of providing a hybrid port which includes a metallic reservoir, a non-metallic cowl and a non-metallic base, where the non-metallic cowl and the non-metallic base jacket the reservoir. The hybrid port is then implanted within biological tissue where a catheter is attached thereto.

BRIEF DESCRIPTION OF THE DRAWINGS

FIG. 1 is a perspective view of a hybrid port according to a first preferred embodiment of the present invention.

FIG. 6 is an enlarged top plan view of the port of FIG. 1.

DETAILED DESCRIPTION OF THE PREFERRED EMBODIMENTS

Figure 2:
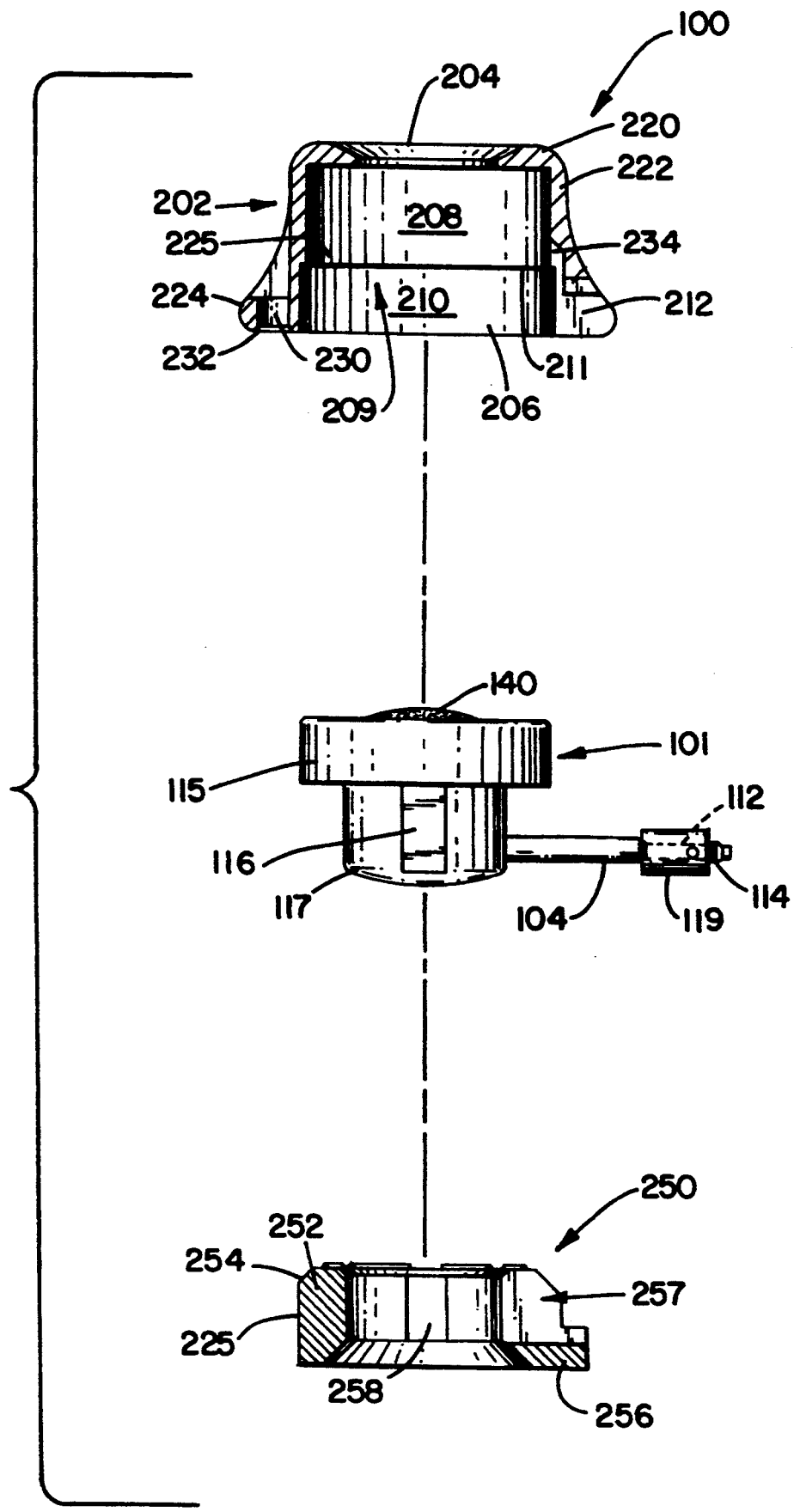
FIG. 2 is an exploded side view of the port of FIG. 1 with portions shown in cross section.

The hybrid port of the present invention provides both benefits associated with an all-metal port and benefits associated with an all-plastic port. The hybrid port of the present invention generally includes a metallic reservoir including a sealed septum, and an internal chamber accessible through the septum, and a non-metallic jacket around the reservoir.

The reservoir includes a chamber sealed by, and accessible through a septum. An outlet tube assembly is operable in connecting the chamber to a catheter which functions to deliver medicants to a desired location.

The reservoir is surrounded by a two piece plastic jacket. While the exact configuration of the two piece jacket can vary, a preferred form includes an outer cowl and a base connected to one another around the reservoir. The outer cowl has a first open end and a second open end. A raised ridge is positioned adjacent the first open end of the outer cowl. The outer cowl further includes a lumen between its first and second open ends having a first and second associated diameter separated by a ridge. The reservoir is positioned within the lumen so that the septum of the reservoir is accessible through the first open end of the outer cowl. The outer cowl also includes a downward positioned outlet tube slot. The outlet tube assembly of the reservoir is positioned in the slot of the outer cowl.

A generally cylindrical base including an upward positioned outlet tube slot extension having an upward positioned slot, fits between the outer cowl and the reservoir. The downward outlet tube slot of the outer cowl mates with the upward slot of the outlet tube slot extension to form an aperture and capture the outlet tube assembly. The base and outer cowl define a forming zone proximate the ridge in the lumen of the outer cowl. The base and outer cowl are connected at the forming zone.

Referring now to the drawings, in which like elements are numbered alike in the various figures, various embodiments of a hybrid port of the present invention are shown.

Figure 5:
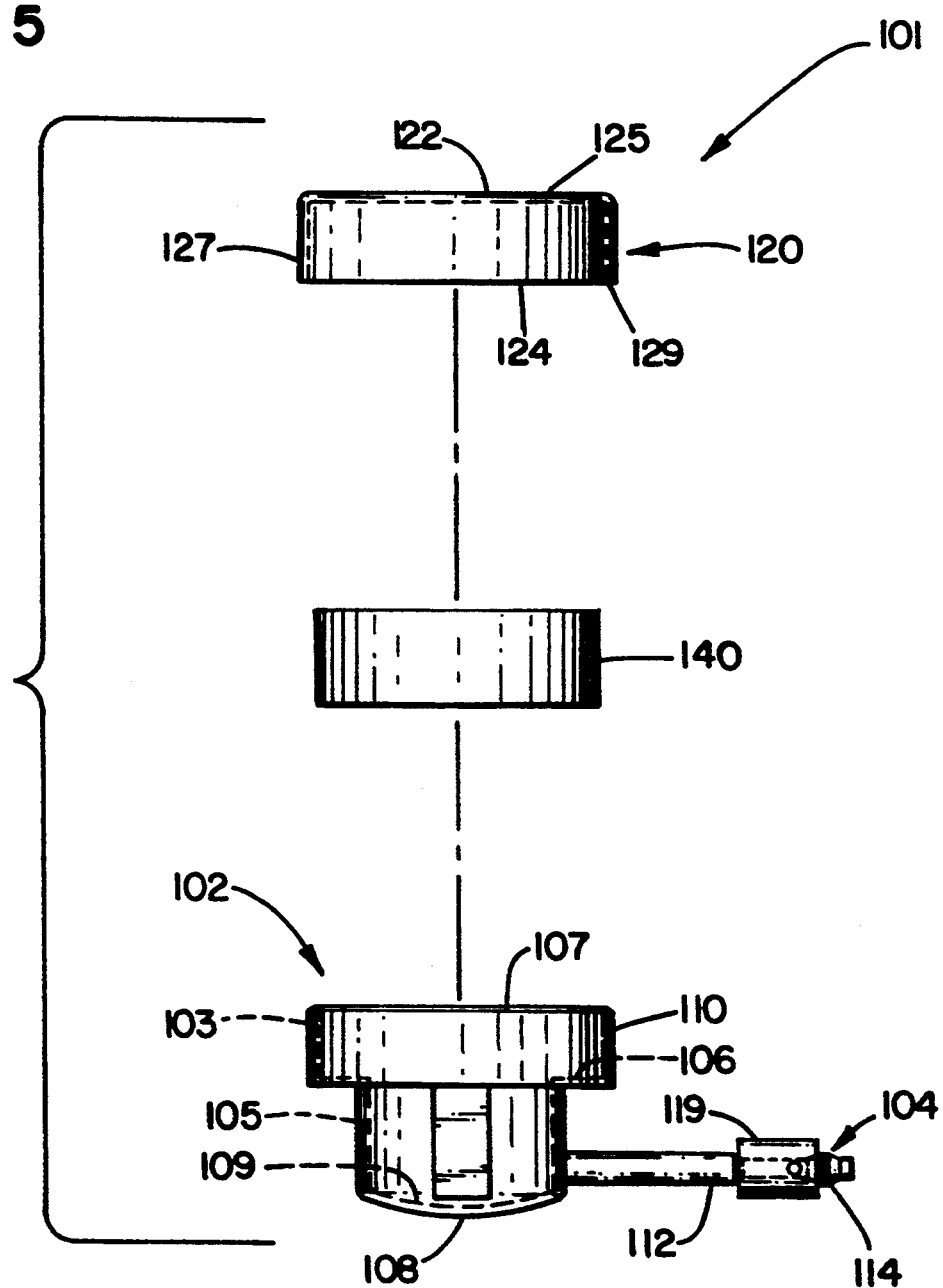
FIG. 5 is an exploded side view of the reservoir of the port shown in FIG. 2.
Figure 7:
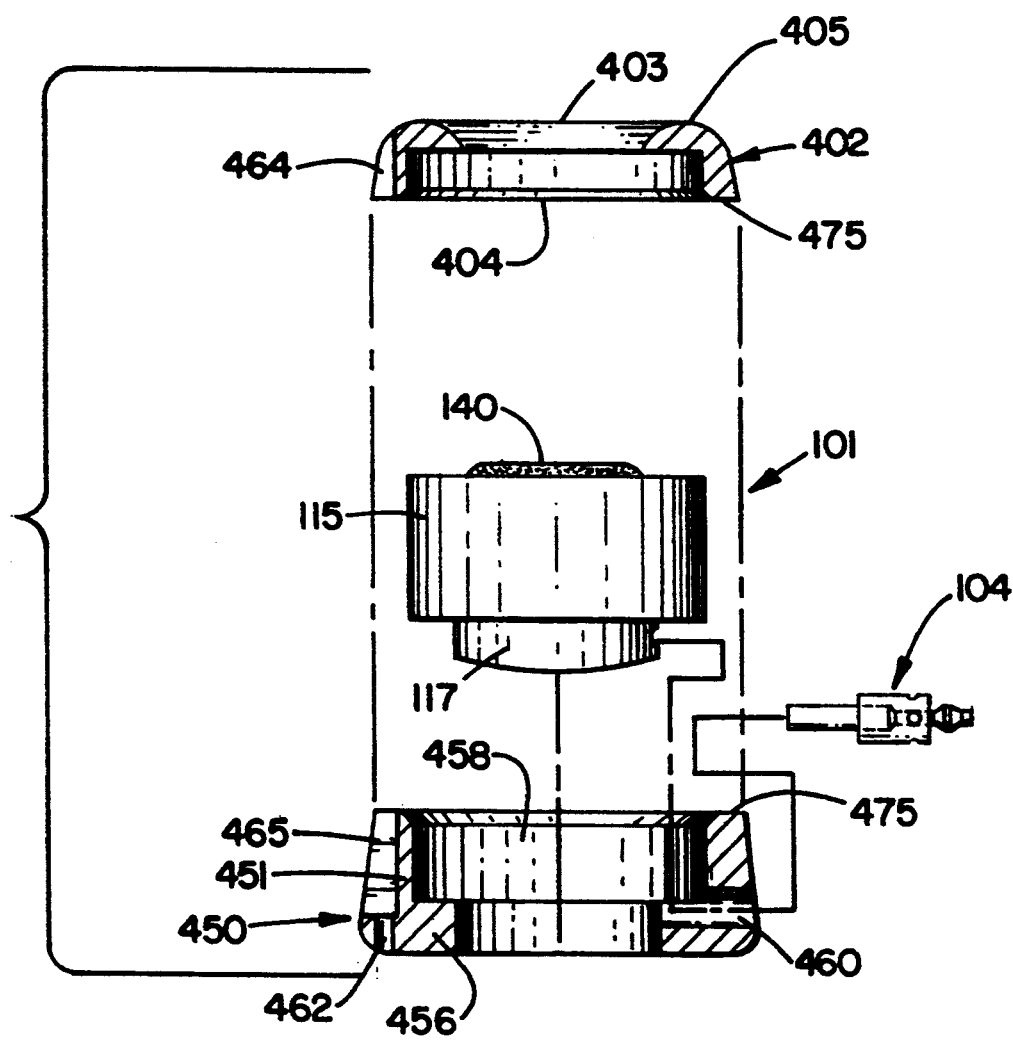
FIG. 7 is an exploded side view of a second preferred embodiment of a hybrid port showing an alternative construction for the two piece jacket with portions shown in cross-section.

Specifically referring to FIGS. 1, 2, and 5 a first embodiment of a hybrid port 100 including a metallic reservoir 101 are shown. Metallic reservoir 101 is preferably constructed from a biocompatible material such as titanium or stainless steel. Reservoir 101 is constructed from a cup 102 including an outlet tube assembly 104, a cap 120 and a wafer-like septum 140 captured therebetween. Both cap 120 and cup 102 include thin-walled construction and are generally cylindrical in configuration.

Cup 102 includes an upper portion 103 and a lower portion 105 separated by a septum shelf 106. Both upper portion 103 and lower portion 105 are cylindrical in configuration and each include inner and outer diameters. Preferably lower portion of cup 102 includes a pair of flats 116, each positioned 180 degrees apart. The diameters of the upper portion 103 are greater than those of the lower portion 105 and septum shelf 106 is formed therebetween. Further, cup 102 includes an open end 107 and a closed end 108.

A chamber 109 is positioned within the lower portion 105 of cup 102. Chamber 109 includes rounded interior side walls to prevent stagnation of fluid in the assembled reservoir 101. Stagnation of fluid is caused by what is known in the medical or fluid arts as dead zones. The rounded interior side walls preferably form a radius which allows an access needle (not shown) to be completely inserted into chamber 109. An outlet tube assembly 104 extends from the lower portion 105 of cup 102.

Outlet tube assembly 104 operates to capture an end of a catheter (not shown) which is placed within the patient. The catheter may be placed in the patient using any of a number of standard techniques. Outlet tube assembly 104 itself may be of the type as referenced in either of U.S. Pat. Nos. 4,723,948 or 4,880,414, the disclosures of which are herein incorporated by reference. Additionally, outlet tube assembly 104 may be of the type described in concurrently filed application entitled "Catheter Connector and Method for Portal Assembly," the drawings and specification of which are incorporated herein by reference.

The outlet tube assembly 104 shown in FIGS. 1, 2 and 5–8 is described in U.S. Pat. No. 4,880,414 and generally includes an outlet stem 112 having a radial enlargement 114 and a retainer sleeve 119 that slidably encircles stem 112. As shown in FIGS. 2 and 5, sleeve 119 is positioned adjacent radial enlargement 114. Outlet tube assembly 104 ensures fluid tight capture of the catheter (not shown). While the outlet tube assembly 104 is advantageous, it should be understood that the present invention is not limited to any particular type of outlet tube assembly, and any of a wide variety of outlet tube assemblies other than those which are incorporated herein by reference, are included within the scope of the present invention.

Wafer-like septum 140 is positioned on septum shelf 106. Preferably wafer-like septum 140 is constructed from silicone. Silicone is a common elastomeric resealable construction and is used throughout the ported industry. Wafer-like septum 140 is cylindrical and has two flat opposed surfaces.

Cap 120 includes a first open end 122 and a second open end 124 positioned between a continuous side wall 127. A flange 125 is positioned at first open end 122. Second end 124 of cap 120 includes an inner diameter and an outer diameter. The difference between the inner and outer diameters is twice the wall thickness of the metallic construction of cap 120. The inner diameter of second open end 124 of cap 120 is slightly less than the outer diameter of upper portion 103 of cup 102.

The metallic wall construction surrounding second open end 124 of cap 120 includes an inside beveled edge 129. Beveled edge 129 permits cap 120 to be forced over upper portion 103 of cup 102. Forcing cap 120 over cup 102 operates to radially and axially compress the wafer-like septum 140. Specifically, side wall 127 of cap 120 forces side wall 110 of cup 120 into septum 140, which radially compresses wafer-like septum 140. Completely forcing cap 120 down upon cup 102 permits flange 125 associated with open end 122 of cap 120 to axially compress septum 140 against septum shelf 106.

When cap 120 has been forced onto cup 102 reservoir 101 is formed. Reservoir 101 includes chamber 109, within the lower portion of cup 102, which is accessible through septum 140. Septum 140, in its compressed state, bulges into chamber 109 on one of its sides, and away from chamber 109 on its other.

The above-described reservoir 101 utilizes what is generally known as an interference fit septum. Septums engaged in the fashion above described can be punctured up to 2,000 times and still reseal the chamber within the reservoir. It should be understood that numerous other techniques are available to connect cap 102 to cup 120 in order to compress septum 140, and the invention is not limited to a specific construction. For example, cap 120 may include threads which can be screwed to threads located on upper portion 103 of cup 102. Cap 120 may be snap fit onto cup 102 to compress septum 140. Additionally, it is possible to weld cap 102 to cup 102 through either spot welding or TIG welding. Cap 120 can fit over or into cup 102 to compress septum 140.

Once assembled, reservoir 101 is a functional structure which holds septum is operable compression for subsequent access to chamber 109 of reservoir 101 via an access needle (not shown).

The outer configuration of assembled reservoir 101 generally includes upper and lower cylindrical portions, 115 and 117. Continuous side wall 127 of cap 120 deforms slightly when forced over upper portion 103 of cup 102, and therefore, upper portion 115 of reservoir 101 includes an outer diameter substantially equivalent to that of the outer diameter of cap 120. Because lower portion 105 of cup 102 is not deformed, lower portion 117 of reservoir 101 has identical dimensions as the lower portion 105 of cup 102.

Figure 3:
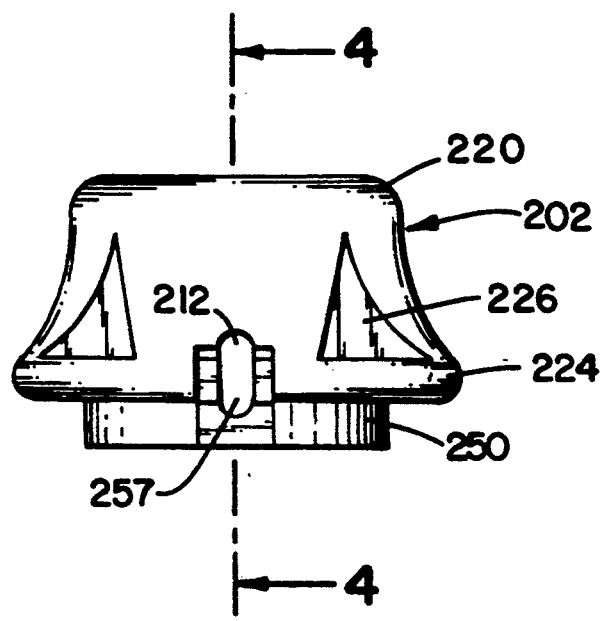
FIG. 3 is a front view of a cowl and a base, excluding a metallic reservoir, of the hybrid port shown in FIG. 1 partially engaged to show cooperation of a slot in the cowl and a slot in the base.
Figure 4:
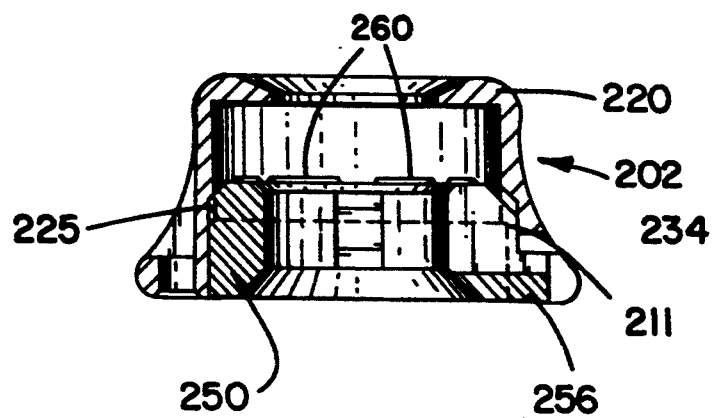
FIG. 4 is a cross-sectional view taken along the line 4—4 in FIG. 3 with the cowl and the base pushed together.

Referring now to FIG. 2, 3 and 4 a two-piece plastic jacket 200 is shown. The first preferred embodiment includes a two piece plastic jacket 200 having an outer cowl 202 and a base 250 which are connected to surround portions of assembled reservoir 101. Both outer cowl 202 and base 250 are constructed from a biocompatible non-metallic substance. The non-metallic substance used to construct outer cowl 202 or base 250 may be a plastic or an elastomeric, or any combination of the two. The first preferred embodiment is constructed from Polysulfone, although other preferred embodiments may be construed from materials such as Pyrolitic Carbon or Glassy Carbon. Pyrolitic Carbon and Glassy Carbon are light in weight, and provide excellent wear resistance. Additionally, these materials provide a hard bottom, and do not produce MRI artifacts.

Outer cowl 202 includes a first open end 204 and a second open end 206 and a lumen 209 positioned therebetween. Lumen 209 includes an upper portion 208 and a lower portion 210. Upper portion 208 of lumen 209 has an associated diameter which is substantially equal to upper portion 115 of reservoir 101. Lower portion 210 of lumen 209 has an associated diameter which is slightly greater than that of upper portion 208. An annular ridge 211 is located between upper section 208 and lower section 210.

Upper portion 115 of reservoir 101 is received within outer cowl 202 so that septum 140 is accessible through first open end 204 of outer cowl 202 as best shown in FIGS. 1 and 2. A ridge 220 on the outer surface of outer cowl 202 aids in locating the septum (as discussed in detail later).

As best seen in FIGS. 2 and 3, outer cowl 202 also includes a downward projecting slot 212. Tube assembly 104 is received within slot 212. Slot 212 generally includes a rounded top surface and two straight side walls.

With reference to FIGS. 2 and 3, base 250 is constructed to attach within lumen 209 of outer cowl 202. Base 250 includes a cylindrical outer side wall 252 having a diameter substantially equal to the inner diameter of the lower portion 210 of lumen 209. Base 250 includes an upper edge 254 which is beveled. Additionally, base 250 includes a slot extension 256 having an upwardly projecting outlet tube assembly slot 257.

The slot extension 256 projects outward a distance adequate to mate with downward projecting slot 212 of outer cowl 202 as best shown in FIG. 4. Slot extension 256 fits within a groove 234 so that base 250 can be fitted into cowl 202 and slot extension 256 can operate with cowl 202 to capture outlet tube assembly 104. Additionally, slot 257 of base 250 cooperates with slot 212 of outer cowl 202 to form an aperture which operates to capture tube assembly 104, as best seen in FIG. 3.

As best seen in FIG. 2, hybrid port 100 is assembled by aligning septum 140 of reservoir 101 with lumen 209 so that the septum 140 of reservoir 101 is exposed through first end 204, and tube assembly 104 is received in slot 212. Base 250 is then inserted within outer cowl 202 adjacent lower portion 117 of reservoir 101 and lower portion 210 of outer cowl 202. The upwardly projecting outlet tube slot 257, on outlet tube extension 256 of base 250 is aligned with tube assembly 104 of reservoir 101 so that the two slots cooperate to form an aperture having the tube assembly captured therein.

Additionally, the interior of base 250 includes a pair of flats 258 positioned 180 degrees apart, which mate with flats 116 of reservoir 101. The mating flats assist in keeping the reservoir from rotating in the base.

Referring to FIGS. 3 and 4, during assembly, base assembly 250 is forced up into outer cowl 202 so that the outer side wall 252 of the base is forced over annular ridge 211 of lumen 209 and into smaller upper section 208 of outer cowl 202. Outer cowl 202 contacts base 250 proximate ridge 211 to define a forming zone, at 225, as best seen in FIGS. 2 and 4. In the first preferred embodiment forcing base 250 over ridge 211 provides an interference fit. In the first preferred embodiment outer cowl 202 and base 250 are further ultrasonically welded at forming zone 225. This arrangement provides a stable sealed fit between outer cowl 202 and base 250. Cowl 202 and base 250 can be connected by solely an interference fit or ultrasonic weld, as well as with one or more snaps, adhesive, solvents, or any combination of the above.

The outer configuration of outer cowl 202 can vary between applications. For example, the dimensions of the ridge may change, height of the cowl may change, and the profile of the cowl may change. Unique outer configurations of the hybrid port are provided for specific applications. For example, different configurations might be suited for: Arterial, inter-spinal, peritoneal, low profile, pediatric venus or TPN applications. The present invention includes methods of assembling a hybrid port including assembling the different configurations listed above.

After hybrid port 100 is subcutaneously implanted within a patient it can be used to facilitate delivery of medicants. The port can also operate to sample blood from a remote area in the body. One preferred configuration of an outer cowl is shown in FIG. 1. The preferred outer configuration of outer cowl 202 includes a ridge 220. Ridge 220 is positioned adjacent first open end 204. Ridge 220 provides a tactile surface which a caregiver locates through palpitation of the skin in order to locate septum 140 of reservoir 101 prior to inserting the access needle (not shown) into hybrid port 100.

A substantially straight side wall 222 extends downward from ridge 220 into a flared annular foot 224. Foot 224 provides a stable surface on which hybrid port 100 rests. Side walls 222 include four depressions 226 positioned equally about outer cowl 202 as best seen in FIGS. 1 and 4. Depressions 226 each terminate at a suture hole 230. Preferably, suture holes 230 each include a beveled edge 232 to facilitate subcutaneous implantation of the hybrid port 100 in the patient.

As shown in FIGS. 2 and 4, base assembly 250 includes crush zones or projections 260 which are used during assembly to assure a secure and proper stack fit between outer cowl 202, reservoir 101, and base assembly 250 in the vertical direction of FIGS. 2 and 4. The crush zones 260 function as spacers without deformation to facilitate a secure fit when the components are manufactured at one dimension in the range of acceptable tolerances. The crush zones 260 are deformable when the components are manufactured at one of the other dimensions in the range of acceptable tolerances. The net effect is that port 100 has a secure mating of components and a more consistent vertical height. Crush zones 260 can have a variety of different shapes including triangular in cross-section for example.

Variations of the two piece jacket construction of port 100 are also possible. For example, the jacket construction may include a top cowl 402 and a lower base 450 as best seen in the second preferred embodiment shown in FIGS. 7 and 8. Top cowl 402, includes a septum opening 403 and a reservoir opening 404. A ridge 405 is positioned annularly around and adjacent to septum opening 404 of top cowl 402. Ridge 405 serves the same purpose as ridge 220 described above.

Base 450 includes a continuous side wall 451 having a lumen 452 positioned between a reservoir retainer 456 and a reservoir opening 458. The inner dimensions of lumen 452 are such that they mate with the lower portion 117 of reservoir 101. Base 450 receives reservoir 101 so that top cowl 402 can mate with upper portion 115 of reservoir 101 and reservoir opening 458 of base 450 can contact the reservoir opening 404 of top cowl 402, to define a forming zone at 475.

Top cowl 402 and base 450 are then connected at forming zone 475 by an ultrasonic weld, snaps, adhesive, solvent, or any other technique or combination thereof. An outlet tube assembly is inserted through a hole 460 in base 450 and into reservoir 101 so that a catheter (not shown) could be attached to the outlet tube assembly to deliver medicants to a remote location in the body, or to remove blood from the patient.

Figure 8:
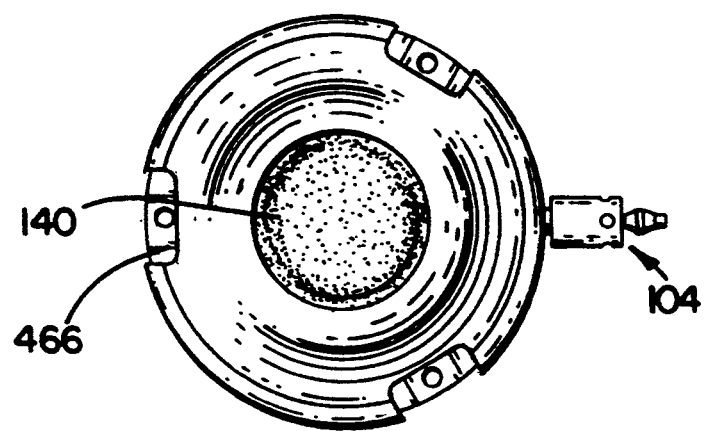
FIG. 8 is a top plan view of the assembled port of FIG. 7.
Figure 9:
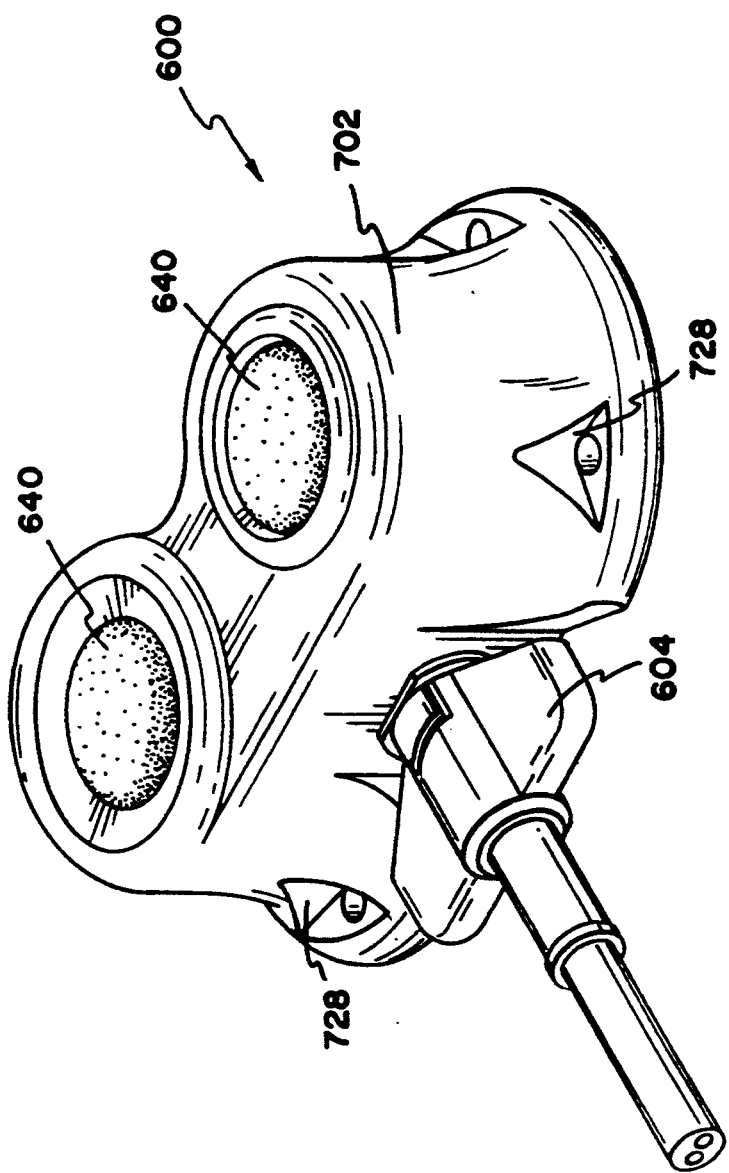
FIG. 9 is a perspective view of a dual hybrid port according to a third preferred embodiment of the present invention.

Base 450 includes a partial indent 465 and suture holes 462. Cowl 402 also includes a partial indent 464. When Base 450 and cowl 402 are connected indents 464,465 mate to form an indent 466 in jacket as best seen in FIG. 8.

Figure 10:
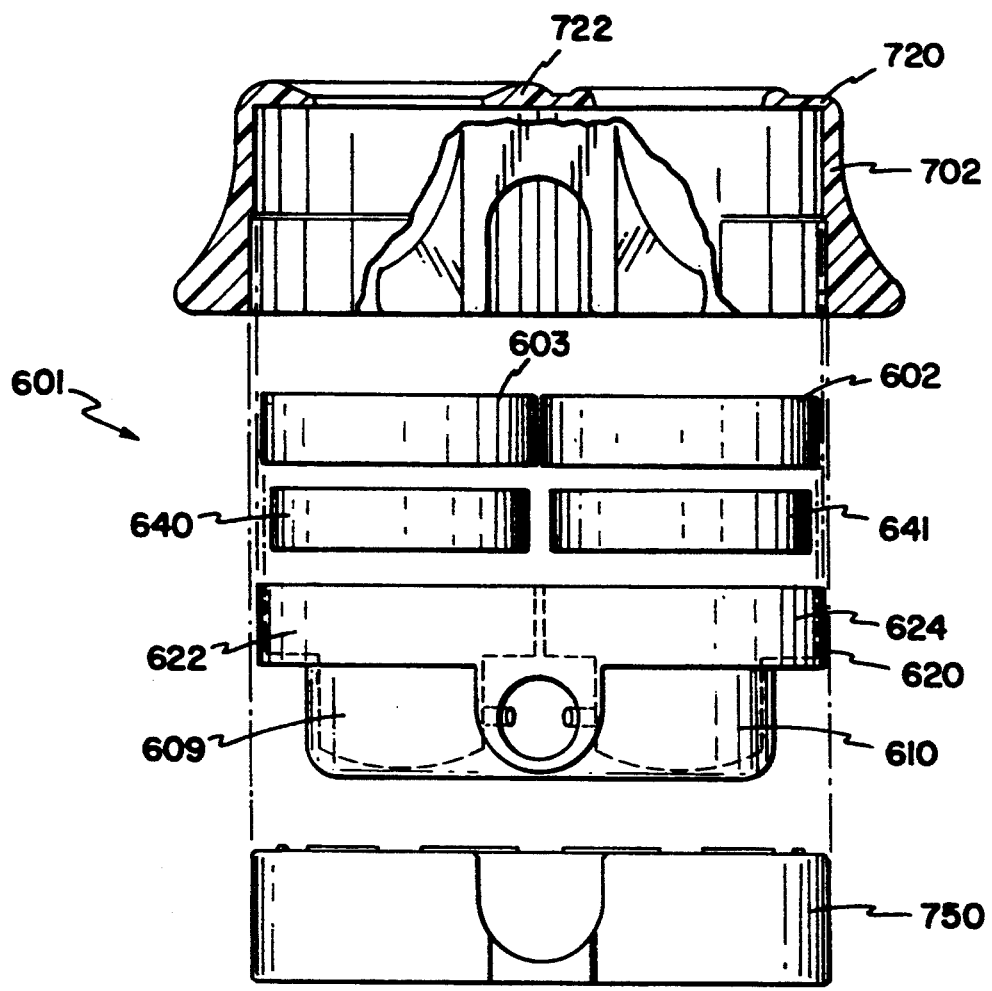
FIG. 10 is an exploded front view of the dual hybrid port of FIG. 9, with portions shown in cross section and with the outlet tubes, the connector, and the catheter removed.

Additionally, a dual hybrid port may be constructed. The preferred dual hybrid port is constructed in accordance with the third preferred embodiment shown in FIGS. 9–16 wherein a single piece non-metallic outer cowl 702 includes a plurality of chambers and one outlet tube slot. A non-metallic base 750 would also be provided. Base 750 could be either single piece as shown in FIG. 10, or two separate pieces. Dual hybrid cowl 702 and base 750 would jacket either a single piece two cap metallic reservoir or two separate sealed metallic reservoirs.

Referring to FIG. 10, metallic reservoir 601 includes a single piece cup 620 having two distinct upper portions 622 and 624. Two caps, 602, 603 engage with upper portions 622 and 624 to radically and axially compress two different septums 640 and 641. Preferably, each cap 602 would be forced into each upper portion 622 and 624 of cup 620 to compress septums, 640 and 641. Cup 620 includes thin walled construction and each upper portion 622 and 624 includes an associated inner diameter. Caps 602 and 603 of the reservoir 601 are preferably of thin walled construction and include associated outer diameters which are slightly greater than the associated inner diameters of the upper portion 622 and 624.

When caps 602 and 603 are forced into each upper portion 622 and 624 the outer walls of caps 602 and 603 are deformed as to force them to radially compress septums 640 and 641. Septums 640 and 641 are axially compressed in the same fashion as for the single reservoir shown in FIG. 5 and described above. Caps 602 and 603 may also be connected to cup 620 through threads, snaps, welding or any other suitable mechanism to compress septums 640 and 641. Alternatively, cup 620 may include two separate reservoirs of the type illustrated in FIG. 2.

Preferably, reservoir 601, as shown in FIG. 10, is received within cowl 702 in the same general fashion as shown in FIG. 2 and described above. As shown in FIG. 10, single piece base 750 attaches to cowl 702 through an ultrasonic weld. In the alternative, base 750 could be attached to cowl through the use of snaps, an interference fit, adhesives, solvents, or any combination thereof.

Often times the two different chambers of the dual hybrid port will include two different medicants, or be for two different purposes, e.g. one for delivering medicants, and one for sampling blood. Because of these possible differences, cowl 702 of dual hybrid port 600 includes two different ridges 720 and 722, positioned adjacent two septums 640 and 641. Different ridges 720 and 722 preferably are of different heights as to provide different tactile responses so a caregiver could differentiate between the two different chambers.

Outer cowl 702 of dual port 600 also includes a plurality of indents 728 which terminate at suture holes 730. Suture holes 730 may include beveled edges to facilitate subcutaneous placement of dual hybrid port 600.

Figure 11:
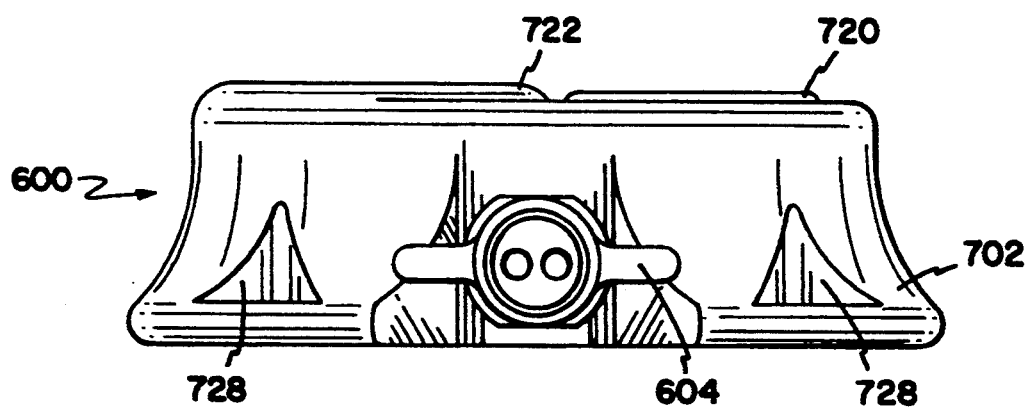
FIG. 11 is a front plan view of the dual hybrid port of FIG. 9.
Figure 12:
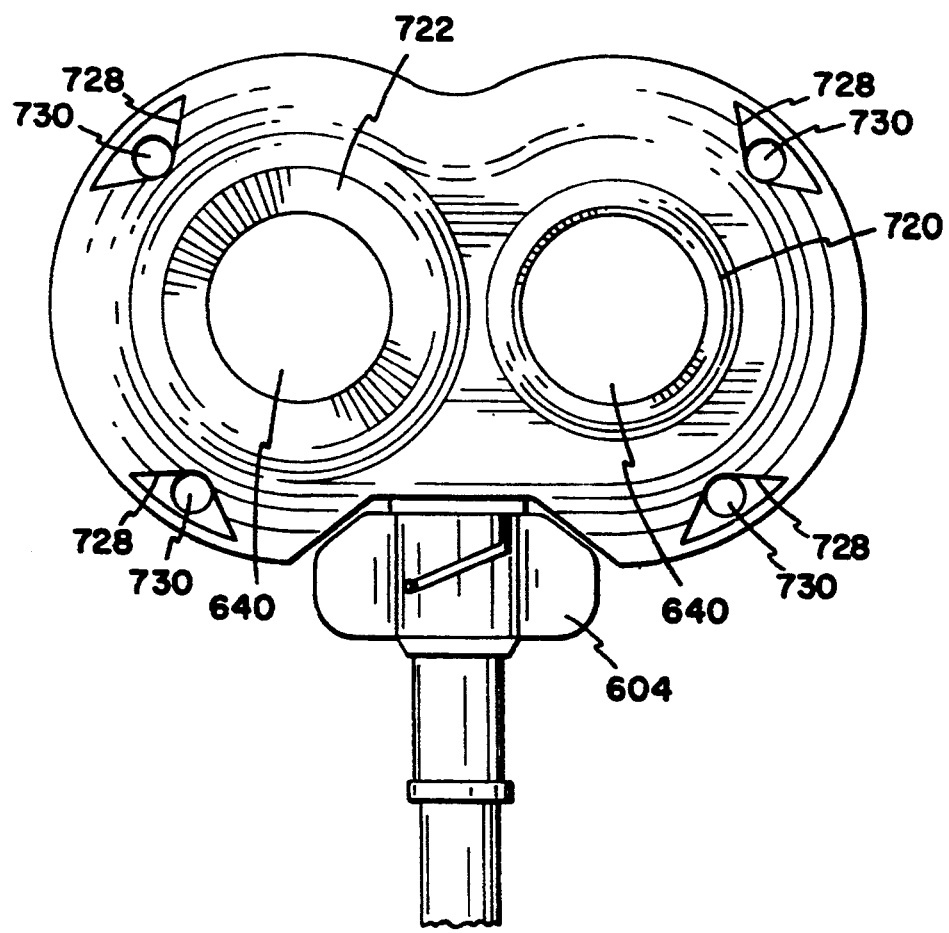
FIG. 12 is a top plan view of the dual hybrid port as shown in FIG. 9.
Figure 13:
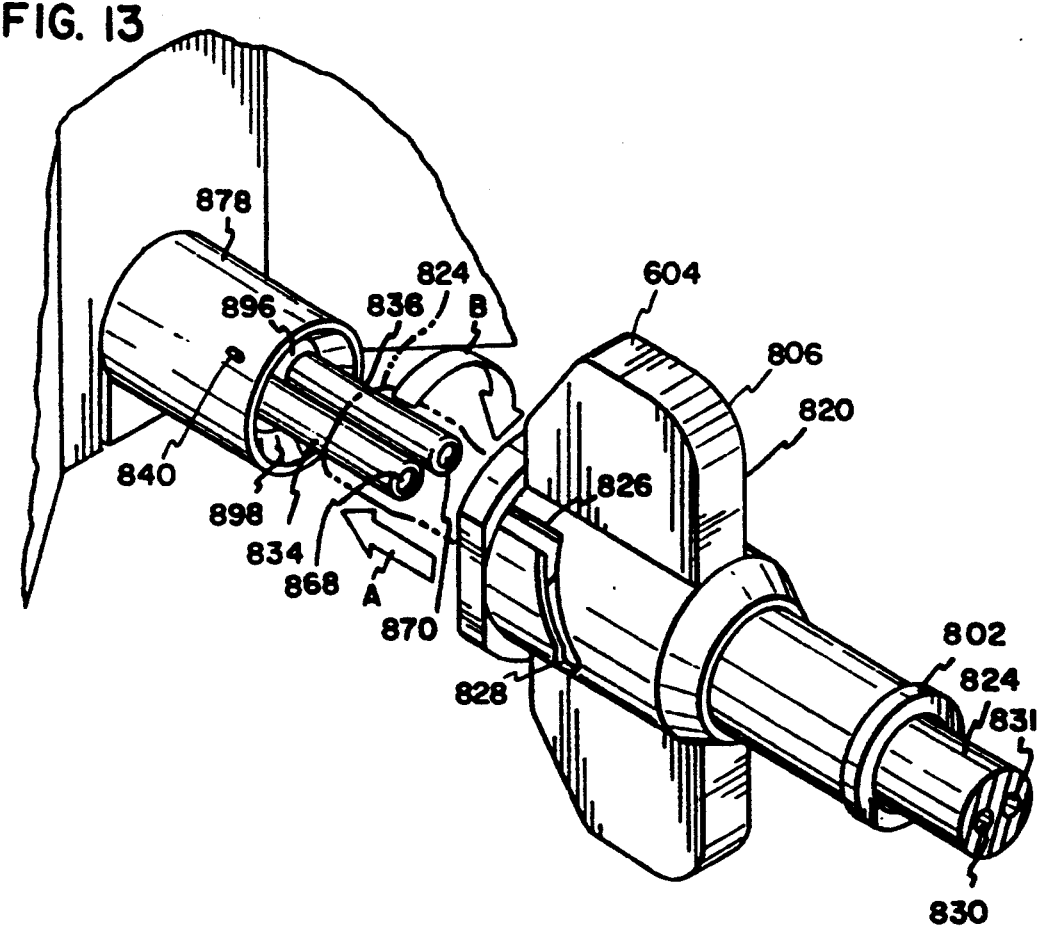
FIG. 13 is a portion of the dual hybrid port of FIG. 9, shown prior to full connection of the catheter to the port.
Figure 14:
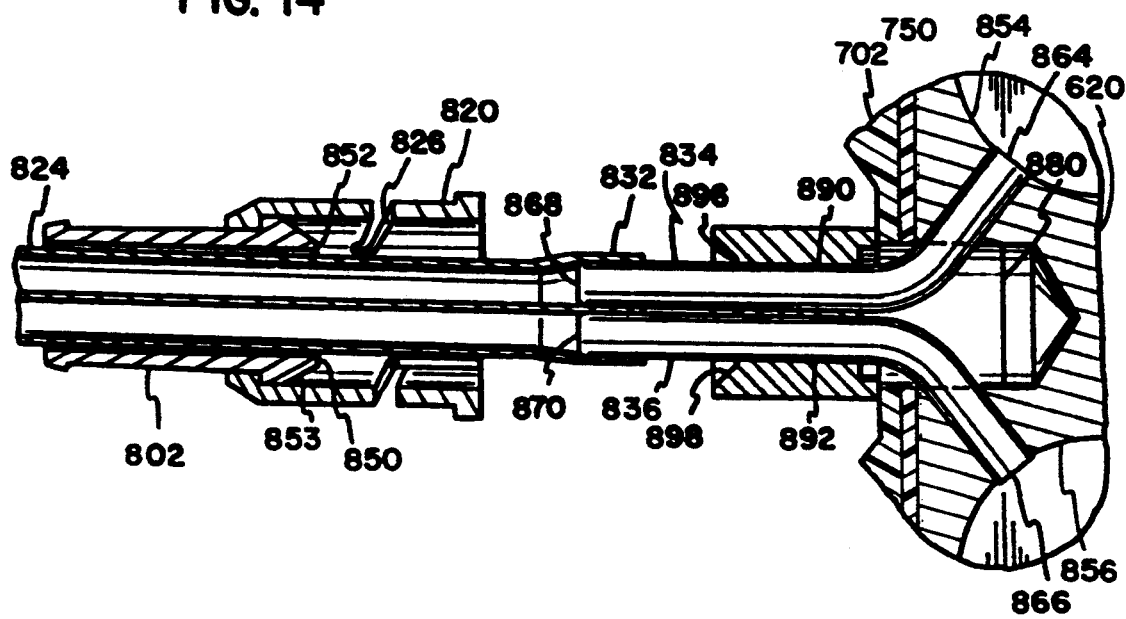
FIG. 14 is a portion of the dual hybrid port of FIG. 9 in partial cross-section in a top view and showing the port prior to full connection of the catheter.
Figure 15:
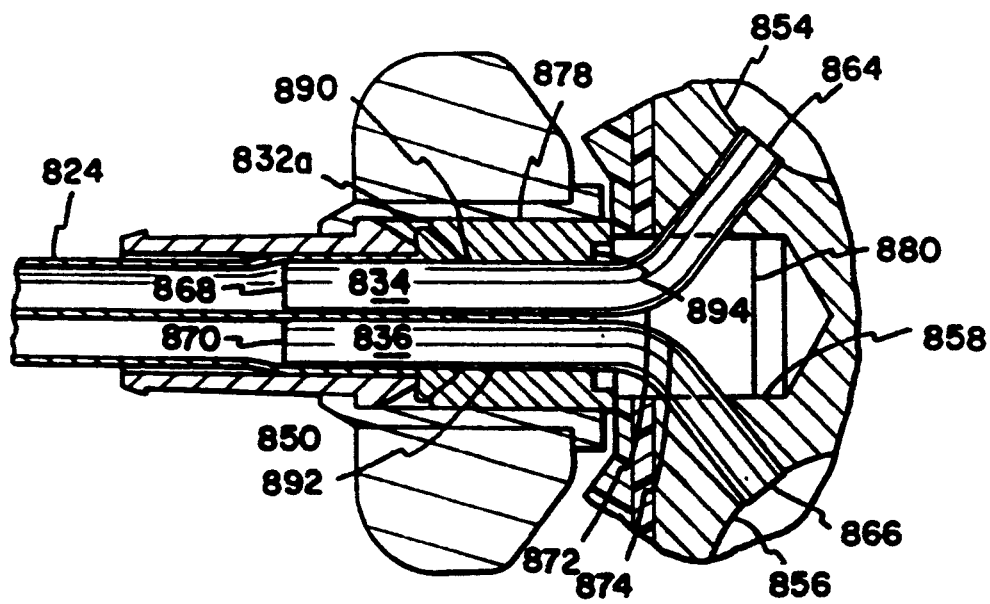
FIG. 15 shows the portion of the port shown in FIG. 14 once the catheter is fully connected.
Figure 16:
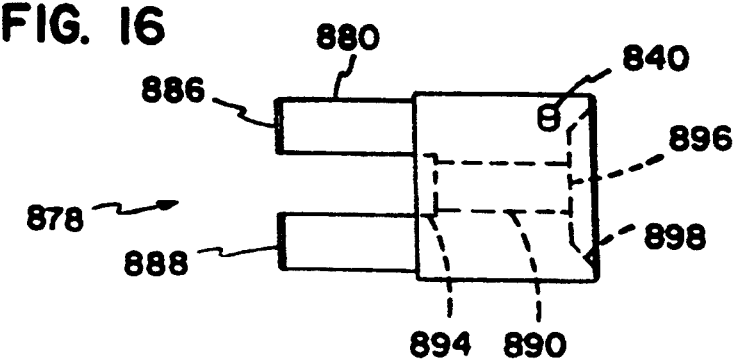
FIG. 16 is an enlarged view of the insert of the dual hybrid port of FIG. 9.

As shown in FIGS. 11 and 12 the dual hybrid port includes an outlet tube assembly 604. In the third embodiment, outlet tube assembly 604 is of the type described in concurrently filed patent application entitled "Catheter Connector and Method of Portal Assembly", the specification and drawings of which have been previously incorporated by reference. Other outlet tube assemblies are possible.

As shown in FIGS. 13–16, outlet tube assembly 604 includes two angled outlet tubes 834, 836 extending from ends 864, 866 positioned at internal chambers 854, 856, respectively, to parallel distal ends 868, 870. An insert 878 with two bores 890, 892 is positioned around a portion of outlet tubes 834, 836. A first portion 880 of insert 878 is positioned within bore 858. Insert 878 includes a planar surface 896 extending generally perpendicular to the longitudinal direction of distal ends 868, 870 of outlet tubes 834, 836. Insert 878 also includes an angled surface 898 diverging away from outlet tubes 834, 836 in a direction away from port 600. End of 880 of insert 878 includes spaced apart portions 886, 888, and a recess 894 for receipt of angled portions 872, 874 of outlet tubes 834, 836.

Sleeve structure 806, including a lock ring 820 and a sleeve 802, draws dual lumen catheter 824 with lumens 830, 831 toward angled surface 898 wherein catheter bunches up and is wedged generally radially inwardly toward outlet tubes 834, 836 to seal the catheter and prevent cross-talk between lummens and also forming a thickened portion 832a of the catheter to hold the catheter to the port. Lock ring 820 is rotatably mounted to sleeve 802 and preferably also slidably mounted in the longitudinal direction. Sleeve 802 preferably includes a tip 850 with a rounded inner surface 852 of lesser inner diameter than a remainder of sleeve 802 for gripping catheter 824, and an angled outer surface 853 for facilitating formation of the thickened portion 832a of catheter 824. A pin 840 and slot 826 mount lock ring 820 to insert 878 through longitudinal movement of lock ring 820 and sleeve 802 in the direction of arrow A in FIG. 13, and also rotational movement of lock ring 820 in the direction of arrow B. The relative rotational mounting of sleeve 802 to lock ring 820 permits lock ring 820 to rotate relative to sleeve 802 to prevent twisting of catheter 824 during use. A detent 828 in slot 826 functions as a positive lock to hold lock ring 820 in the locked position. A second pin and slot arrangement are provided on opposite sides of insert 878 and lock ring 820, respectively. Outlet tubes 834, 836, insert 878, and lock ring 820 are preferably made of metal. Preferably, outlet tubes 834, 836 insert 878 are welded to metallic cup 620. Sleeve 802 is preferably made of plastic and is preferably somewhat flexible to assist in a strain relief function for stresses applied to catheter 824.

The present invention has the advantages that any defects in the outer jacket may be detected before the entire hybrid port is assembled. Detection of defects is not dependent upon total assembly of the hybrid port, which may necessitate disposal of the whole port. During production the plastic parts are checked for defects. If defects are present the individual piece may be discarded.

Additionally, the present invention allows an easy and economical method of constructing hybrid ports of various configurations. As stated earlier, different applications may require different outer configurations of the port. In certain circumstances the ridge may be wider, or taller than others. Also, the annular foot may be increased or decreased in size and the height of the port may be adjusted. By combining the different ridge configurations with different annular feet, and different heights of the outer cowl itself, a variety of special applications can be accomplished, including those applications discussed above.

A method of using the hybrid port is also within the scope of the present invention. While it is not preferred, a caregiver may be provided with the unassembled parts of hybrid port 100. These unassembled parts would include sealed metallic reservoir 101, including outlet tube assembly 104, non-metallic outer cowl 202 and inner base 250. The caregiver would select an outer cowl having the proper outer configuration for the desired application. The caregiver then would assemble hybrid port 100, according to the description above, where outer cowl 202 and inner base 250 are connected by an interference fit or snaps. The caregiver would implant port 100 within the patient, attaching outlet tube assembly 104 to a catheter which has been previously implanted, thus allowing medicants to be delivered to the desired location.

The present invention includes advantages of a metal port and advantages of a plastic port. The outer plastic construction significantly decreases the weight of the present port, as compared to all-metal ports. While the metallic construction of the reservoir provides structure to adequately seal the septum. Additionally, by utilizing a sealed metal reservoir, the present invention provides an adequately sealed chamber which is biocompatible.

Further, it is to be understood that even though numerous characteristics and advantages of the invention have been set forth in the foregoing description, together with details of the structure and function of the invention, the disclosure is illustrative only and changes may be made in detail, and especially in the matters of shape, size and arrangement of parts, wherein the principles of the invention to the full extent indicated by the broad general meaning of the terms in which the appended claims are expressed.

What is claimed is:

1. A hybrid port, comprising:
   a metallic reservoir having an open top, a closed bottom, and a septum sealingly received in said open top, said reservoir further including a chamber accessible through said septum;
   a non-metallic cowl including a septum opening, said cowl further including a flange positioned adjacent said top of said reservoir, said septum being accessible through said septum opening; and
   a non-metallic base including a reservoir opening, said reservoir operably received through said reservoir opening of said base; said base and said cowl being positioned and arranged as to define a forming zone; said base and said cowl connected at said forming zone.

2. A hybrid port as in claim 1 wherein said cowl and said base are connected by an ultrasonic weld at said forming zone.

3. A hybrid port as in claim 2 wherein said cowl and said base are connected by an interference fit at said forming zone.

4. A hybrid port as in claim 1 wherein said cowl and said base are connected by an interference fit at said forming zone.

5. A hybrid port as in claim 1 further comprising an outlet tube assembly in fluid communication with said chamber of said reservoir.

6. A hybrid port as in claim 5 wherein said reservoir is constructed out of titanium.

7. A hybrid port as in claim 1 wherein said cowl and said base are constructed from plastic.

8. A hybrid port as in claim 7 wherein said cowl and said base are constructed out of polysulfone.

9. A hybrid port as in claim 1 wherein said base includes a plurality of suture holes so that said hybrid port can be sutured to a subcutaneous layer.

10. A hybrid port as in claim 8 wherein said chamber of said reservoir includes a rounded bottom.

11. A hybrid port as in claim 1 wherein said reservoir further comprises:
 a generally cylindrical metal cup including an open end and a closed end, said cup further including a septum seat between said open end and said closed end; said septum disposed in said open end of said cup proximate said septum seat;
 a cap having a first opening and a second opening, said cap further including continuous side wall between said first and second openings, and a flange proximate said second opening, said cap fitted to said cup so that said septum is radially compressed by said continuous side wall and axially compressed between said flange and said septum seat.

12. A hybrid port as in claim 11 wherein said base further includes a pair of flats positioned adjacent said cup of said reservoir, and said cup includes a pair of flats operable in contacting said flats of said base to keep said reservoir from rotating.

13. A hybrid port as in claim 1 further comprising a catheter connector.

14. A hybrid port as in claim 1 including two of said metallic reservoirs; two of said cowls; and two of said bases interconnected to define a dual chamber hybrid port.

15. A hybrid port, comprising:
 a metallic reservoir including a chamber; said reservoir sealed by and accessible through a septum;
 a non-metallic outer cowl including a septum opening, a reservoir opening and a lumen positioned therebetween, said cowl further including a flange positioned adjacent to said septum opening and an inner ridge positioned within said lumen, said septum of said reservoir being accessible through said septum opening; and
 a non-metallic inner base including a reservoir opening, said base further including an outer wall; said base being retained within said lumen of said outer cowl to define a forming zone proximate said ridge of said lumen of said cowl, and said cowl and base are attached at said forming zone to form a jacket about said reservoir.

16. A hybrid port as in claim 15 wherein said outer cowl and said inner base are attached with an ultrasonically weld at said forming zone.

17. A hybrid port as in claim 15 further comprising an outlet tube assembly fluidly connected to said reservoir, said outlet tube assembly operative in mating with a catheter, said base of said hybrid port including a slot extension protruding therefrom and having an upwardly projecting slot operable in mating with a downward slot associated with said cowl to form an aperture so that said aperture captures said tube assembly.

18. A hybrid port as in claim 15 wherein said reservoir includes a first flat and said base includes a second flat so that said first flat seats with said second flat to align said reservoir.

19. A hybrid port as in claim 15 wherein said reservoir defines a chamber having a radial bottom.

20. A hybrid port as in claim 15 wherein said outer cowl further includes:
 a ridge positioned adjacent said septum opening, and;
 an annular foot positioned adjacent said reservoir opening.

21. A hybrid port as in claim 20 wherein said annular foot includes a plurality of suture holes.

22. A hybrid port as in claim 21 wherein said suture holes include beveled edges.

23. A hybrid port as in claim 22 wherein said cowl includes a plurality of depressions located between said ridge and said foot above said suture holes.

24. A dual chamber hybrid port, comprising:
 a metallic reservoir including two chambers, each accessible through a discrete septum;
 a non-metallic cowl including a pair of discrete septum openings, said cowl further including a pair of flanges, each of said flanges positioned adjacent to one of said septums so that each of said septums is accessible through one of said septum openings; and
 a non-metallic base including a reservoir opening, said reservoir operably received through said reservoir opening of said base, and said cowl being positioned and arranged with said base as to define a forming zone; said base connected to said cowl at said forming zone.

25. A dual hybrid port as in claim 24 wherein said non-metallic cowl includes a lumen having a ridge disposed therein; and said base fits within said lumen between said reservoir and said cowl so that said forming zone is positioned proximate said ridge of said lumen of said cowl.

26. A dual hybrid port as in claim 25 wherein said cowl further includes an annular foot distal from said septum opening.

27. A dual hybrid port as in claim 26 wherein said annular foot includes a plurality of suture holes.

28. A dual hybrid port as in claim 27 wherein said suture holes include beveled edges.

29. A dual hybrid port as in claim 24 wherein said pair of flanges of said cowl each includes a ridge.

30. A dual hybrid port as in claim 29 wherein said ridges of said flanges are of different configurations.

31. A dual hybrid port as in claim 24, further comprising a catheter connector.

32. A dual hybrid port, comprising:
 a first metallic reservoir including a first chamber accessible through a first sealed septum;
 a second metallic reservoir including a second chamber accessible through a second sealed septum;
 a non-metallic cowl including a pair of septum openings and a pair of reservoir openings, said cowl further including a flange positioned adjacent said septum opening, each of said septums accessible through one of said septum openings;
 a first non-metallic inner base including a reservoir opening, said first reservoir received within said reservoir opening of said first inner base, said base retained within said cowl between said first reservoir and said cowl to define a first forming zone, said first inner base connected to said cowl at said first forming zone;
 a second non-metallic inner base including a reservoir opening, said second reservoir received within said reservoir opening of said second inner base, said base retained within said between said second reservoir and said cowl to define a second forming zone, said second inner base and said cowl connected at said second forming zone.

33. A method of using a hybrid port comprising the steps of:

providing a hybrid port, said hybrid port including a metallic reservoir having an open top, a closed bottom, and a septum sealingly received in said open top, said reservoir further including a chamber accessible through said septum; a non-metallic cowl including a septum opening, said cowl further including a flange positioned adjacent said top of said reservoir, said septum being accessible through said septum opening; and a non-metallic base including a reservoir opening, said reservoir operably received through said reservoir opening of said base; said base and said cowl being positioned and arranged as to define a forming zone; said base and said cowl connected at said forming zone;

implanting said hybrid port within a patient; and attaching said hybrid port to a catheter to deliver fluids to a desired location within said patient.

34. A method of use as in claim 33 wherein the step of providing a hybrid port further includes the step of attaching said cowl to said base at said forming zone.

* * * * *

UNITED STATES PATENT AND TRADEMARK OFFICE
CERTIFICATE OF CORRECTION

PATENT NO. : 5,387,192

DATED : February 7, 1995

INVENTOR(S) : Glantz et al.

It is certified that error appears in the above-identified patent and that said Letters Patent is hereby corrected as shown below:

```
    In column 5, line 7, "120" should read --102--.
    In column 5, line 24, "102 to cup 120" should read --120 to
cup 102--.
    In column 5, line 29, "102" should read --120--.
    In column 5, line 34, "is" should read --in--.
    In column 9, line 27, "lummens" should read --lumens--.
    In claim 16, lines 2 and 3, "ultrasonically" should read --
ultrasonic--.
    In claim 32, line 21, insert --cowl-- before the word
"between".
```

Signed and Sealed this

Second Day of June, 1998

Attest:

Attesting Officer

BRUCE LEHMAN

Commissioner of Patents and Trademarks